(12) United States Patent
Schlesinger

(10) Patent No.: US 11,793,660 B2
(45) Date of Patent: Oct. 24, 2023

(54) EMERGENCY LIMB FIXATION OR RESTRAINING DEVICE

(71) Applicant: Yoel Schlesinger, Brooklyn, NY (US)

(72) Inventor: Yoel Schlesinger, Brooklyn, NY (US)

( * ) Notice: Subject to any disclaimer, the term of this patent is extended or adjusted under 35 U.S.C. 154(b) by 462 days.

(21) Appl. No.: 15/788,307

(22) Filed: Oct. 19, 2017

(65) Prior Publication Data
US 2018/0161193 A1    Jun. 14, 2018

Related U.S. Application Data

(63) Continuation-in-part of application No. 14/568,344, filed on Dec. 12, 2014, now abandoned.

(60) Provisional application No. 61/915,261, filed on Dec. 12, 2013.

(51) Int. Cl.
*A61F 5/00* (2006.01)
*A61F 5/058* (2006.01)
*A61F 5/01* (2006.01)

(52) U.S. Cl.
CPC .......... *A61F 5/05825* (2013.01); *A61F 5/058* (2013.01); *A61F 5/0585* (2013.01); *A61F 5/05858* (2013.01); *A61F 2005/0158* (2013.01)

(58) Field of Classification Search
CPC .... A61F 5/058; A61F 5/05825; A61F 5/0585; A61F 5/05858; A61F 5/0104; A61F 5/0106; A61F 5/0188; A61F 5/3715; A61F 5/3723; A61F 5/373; A61F 5/05841; A61F 5/05883; A61F 5/05891
USPC .......................................................... 602/20
See application file for complete search history.

(56) References Cited

U.S. PATENT DOCUMENTS

| | | | | |
|---|---|---|---|---|
| 1,136,397 A | * | 4/1915 | Bloch | A61F 5/0585 602/5 |
| 1,295,297 A | * | 2/1919 | French | A61F 5/0123 602/16 |
| 1,374,177 A | * | 4/1921 | Barry | A61F 5/05841 602/16 |
| 2,339,515 A | * | 1/1944 | Parcher | A61F 5/05841 602/20 |
| 3,003,625 A | * | 10/1961 | Anderson | A61F 5/0585 206/349 |
| 4,220,148 A | * | 9/1980 | Lehneis | A61F 5/0123 602/26 |
| 4,982,732 A | * | 1/1991 | Morris | A61F 5/0125 403/96 |
| 8,277,403 B2 | * | 10/2012 | Ceriani | A61F 5/0125 128/846 |
| 2005/0187506 A1 | * | 8/2005 | Reinhardt | A61F 5/0125 602/30 |

(Continued)

*Primary Examiner* — Adam Baker
(74) *Attorney, Agent, or Firm* — Israel Nissenbaum; Yitzy Nissenbaum

(57) ABSTRACT

A method of splinting limbs of a patient by a single person and an elongated splint device, for use in the method. The splint device has a first track member and second and third elongated riding members movably held and positioned on the first track member. The riding members are freely movable on the first track member along a single longitudinal axis to obtain a proper length for splinting and a releasable locking mechanism is included to maintain the selected length. Two or more adjustable belt elements are removably connected to the riding member and serve to affix the splint device to a patient in a proper splinting position.

10 Claims, 16 Drawing Sheets

(56) References Cited

U.S. PATENT DOCUMENTS

2013/0072328 A1\* 3/2013 Williams, Sr. ..... A63B 69/0071
473/450

\* cited by examiner

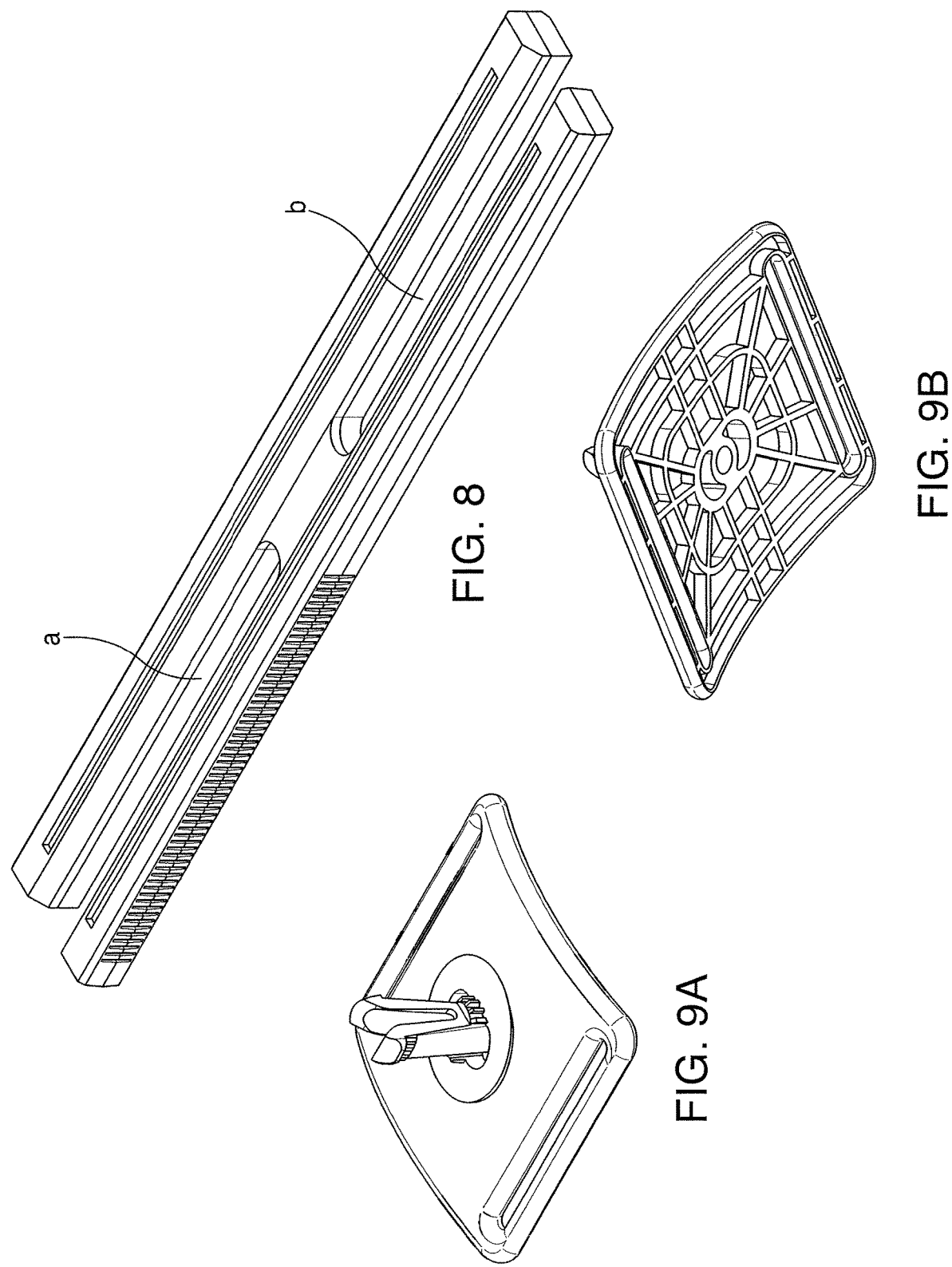

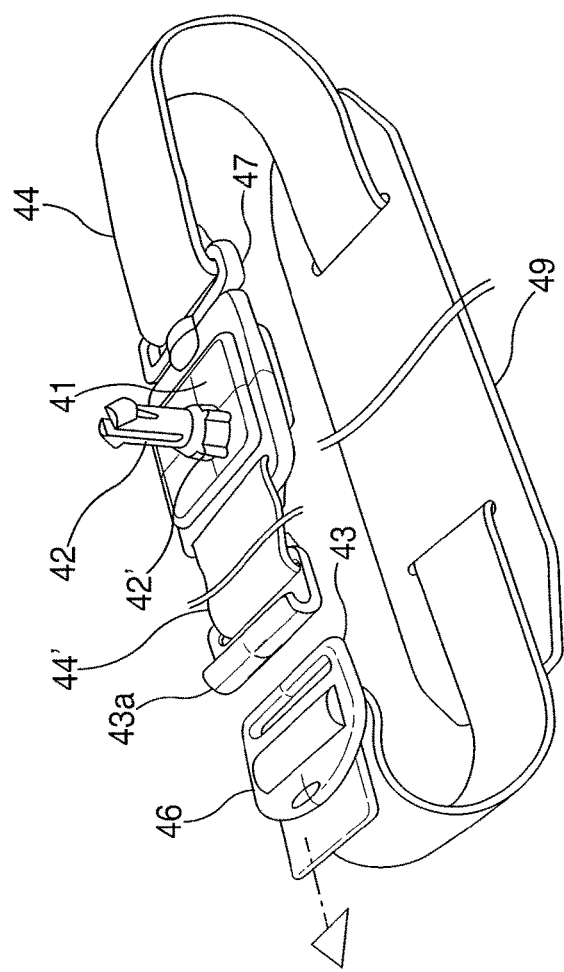
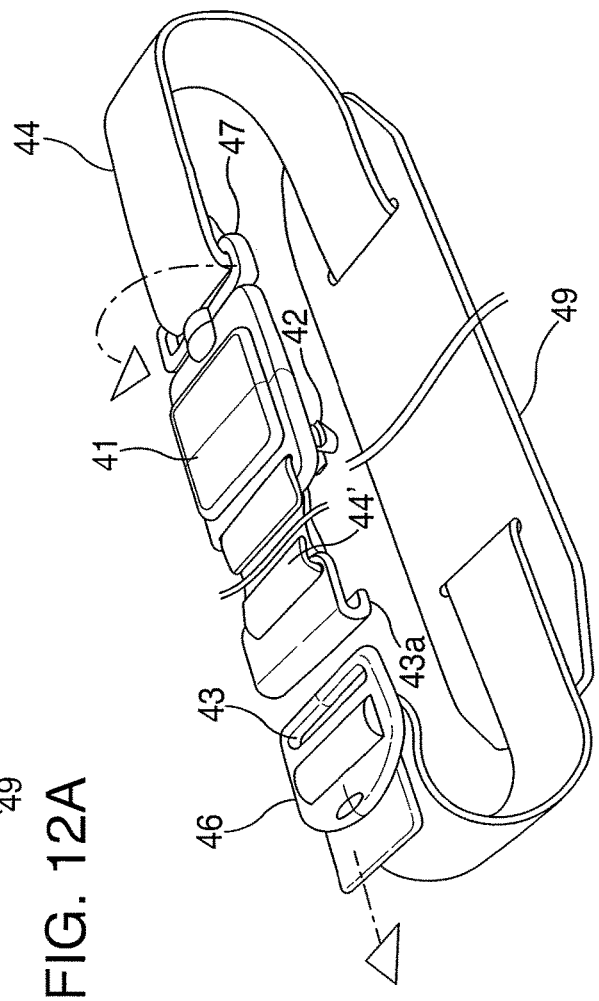

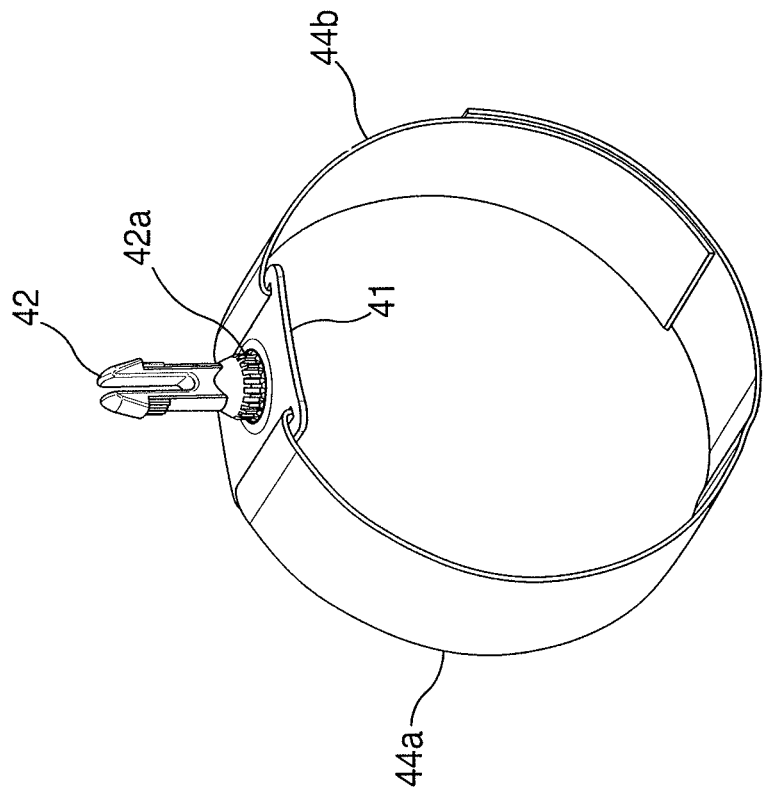
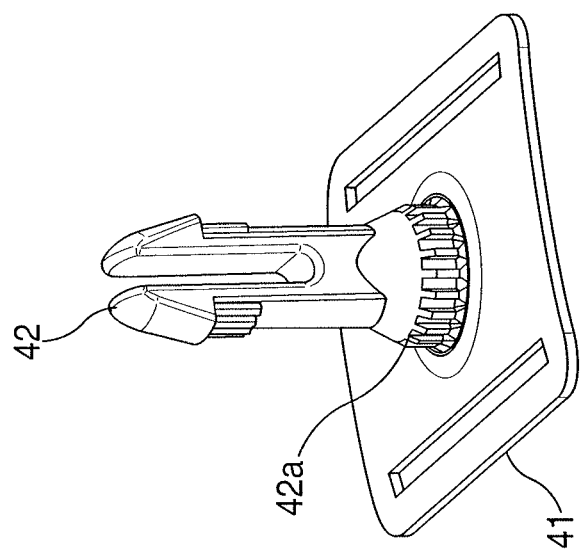
FIG. 14B
FIG. 14A

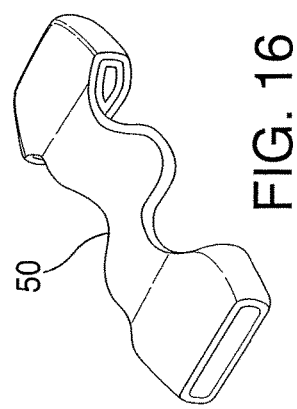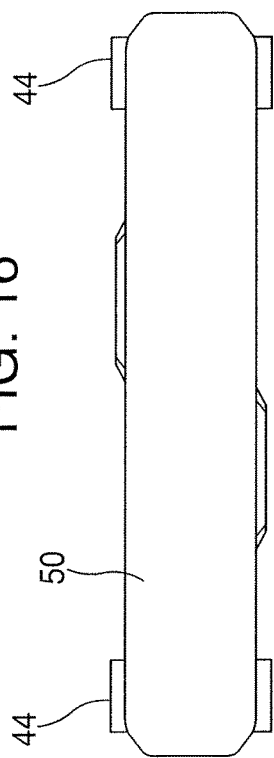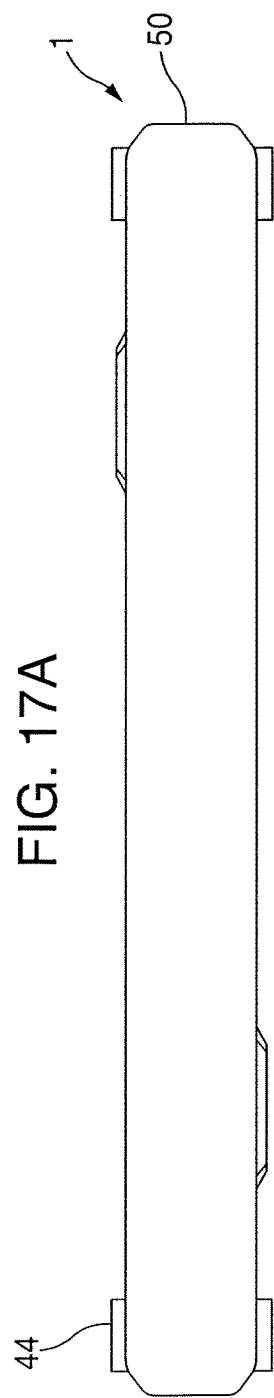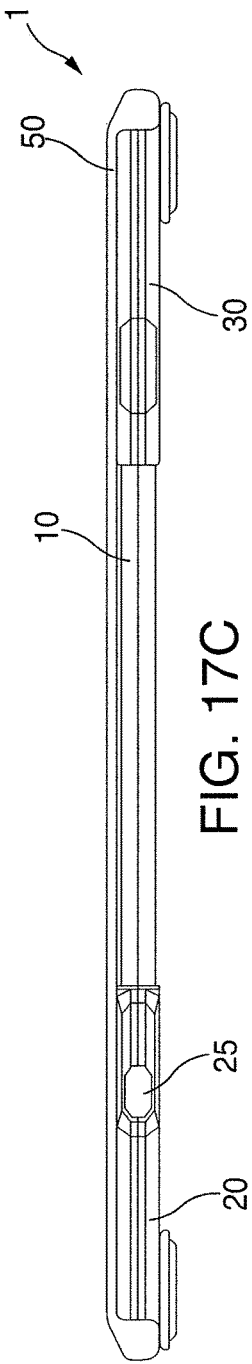
FIG. 16
FIG. 17A
FIG. 17B
FIG. 17C

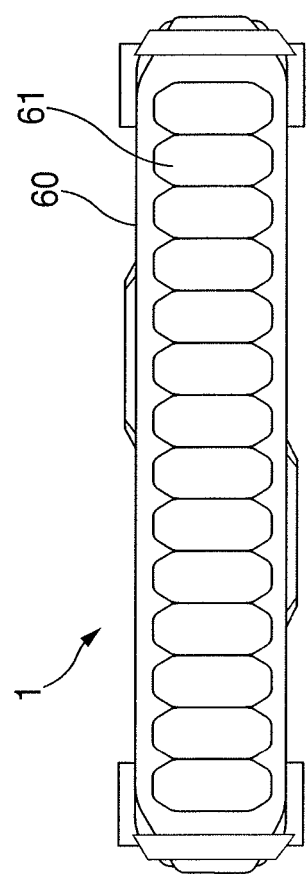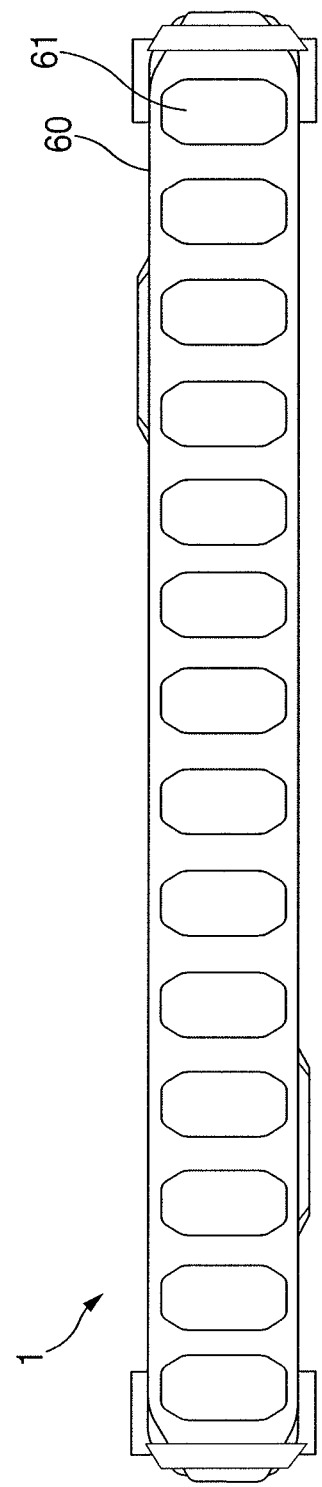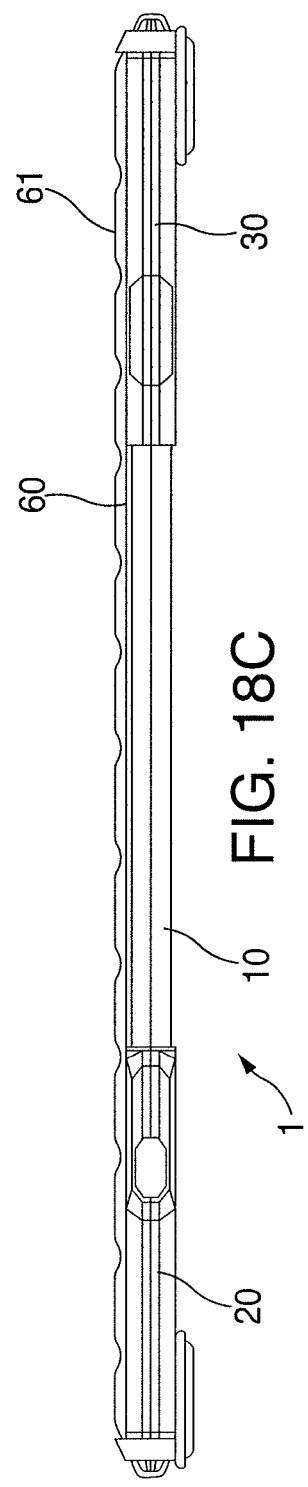

EMERGENCY LIMB FIXATION OR RESTRAINING DEVICE

This application is a continuation in part of U.S. patent application Ser. No. 14/568,344, filed Dec. 9, 2014, the entire disclosure of which is incorporated herein by reference thereto.

FIELD OF THE INVENTION

This invention relates to splints and fixation or restraining devices for preventing increased trauma by restraining movement of limbs or other body parts of living beings including animals and humans and relates particularly to devices for use in emergency field situations for position fixing of arms and legs around elbow and knee joints by EMS personnel.

BACKGROUND OF THE INVENTION

When a person fractures (or breaks) a limb and requires emergency handling and treatment prior to hospitalization, EMS (emergency medical services) or other medical personnel generally must provide rapid and temporary limb immobilization in the condition, as found, in order to ensure that no further injuries and tissue injuries occur. A basic splint used for such emergency purpose is a long wooden board padded with a soft sponge and generally requires a great deal of practice to use properly and even then requires two EMTs (emergency medical technician) for proper placement. The current method and device for fixation of injured limbs, such as after an accident, to prevent aggravation or additional injury and pain is by means of the splint and two tying cloths known as curvets, with a first EMT manually positioning and holding the splint on the patient while a second EMT ties it into position with the curvets.

In a typical situation, for example, the splint is placed across a forearm and upper arm around an elbow for an arm injury. Similarly, the splint is placed across a thigh and shin around a knee for a leg injury. Once the splint is positioned and while arm or leg is maintained in position, ends of the splint are tied with the curvets by utilizing a defined winding and tying procedure to provide both a secure hold and avoiding undue pain to the injured person. Such fixation requires training for proper deployment and involves inordinate amounts of time while an injured person must painfully maintain a non-moving position. The training is standard for EMT and hospital personnel and often requires viewing of videos or hands-on lessons. In addition to the drawbacks recited above, the length of a typical splint is often too large to be carried in a trauma jump bag/kit used by EMTs and requires separate awkward transport.

Many splint devices have been described in the past with cuffs and rotatable pivots, as well as ones with connecting elements, many of which are overly complicated, difficult to operate and utilize, especially in emergency situations and are often made of metal, precluding their use in conjunction with essential diagnostic machinery such as MRI and x-ray machines. In addition, many limb fixation devices are designed for utilization in hospital or clinic settings where immediate immobilization of patients before or during emplacement of a splint is not of a major concern. Accordingly, they are often very expensive and complicated and are not suitable for rapid emergency use with modified procedural deployment.

SUMMARY OF THE INVENTION

It is accordingly an object of the present invention to provide a splint device and method of use thereof for injured limb or body part fixation for animal or human patients for use especially under immediate emergency conditions, which requires little or no training for proper and rapid secure deployment and which may also be used in hospital or clinic settings.

It is a further object of the present invention to provide the splint device and method which is rapidly deployable by a single EMT or other medical personnel and which is compact and readily transportable in a trauma jump bag/kit.

It is a still further object of the invention to provide the splint device which is easy to clean, MRI/x-ray proof, economically disposable and useful as a splint for bent and straight limb fracture utilizations.

In the parent of this application, numerous embodiments of splint devices were disclosed, with the present splint device including various features thereof. Generally, the present invention comprises an improved embodiment over those disclosed in the parent application with the improved features of economy in manufacture, compactness and ready deployability, among other advantages.

The splint device of embodiments herein, are for use primarily under emergency conditions, rather than in a hospital setting (though they are, of course, utilizable in hospital settings as well). The splint device comprises elongated embodiments with an adjustable length or having a fixed length but with adjustable aperture positions for placement and position locking of limb retaining straps, belts or clamps at selected different positions.

Adjustable length splints herein include elongated single axis telescoping splints, and joined parallel splint elements which are movable relative to each other and which are position fixable and lockable at selected lengths. Other adjustable length splints included foldable splints with hinged segments similar to folding wooden rulers and linkable splints having segment attachments to increase or decrease the splint length, as needed.

Fixed length splints herein are provided with numerous points of attachment to the limb retaining straps, belts or clamps, along its elongated length to thereby provide the adjustable length as needed.

Apertures in the splint or splint segments or the straps, belts or clamps, provide the most expeditious means of lockable attachment between cooperative attachment or connecting elements such as nuts and bolts connections. Position locking elements without slippage are desirable for both length retention and against rotational movement between the splint and the straps, belts or clamps to maintain proper splinting application.

The expandable and contractible longitudinally elongated splint device embodiment comprises:

a. at least two telescoping splint elements movably fastened to each other and configured to be movable in a longitudinal direction to obtain a desired length of the elongated splint;

b. a releasable locking element configured to maintain the telescoping splint elements at the desired length;

c. at least two releasable and adjustable limb engaging elements, with each comprising connecting members configured for attachment of the limb engaging elements respectively to the telescoping splint elements in a desired spaced apart position on the telescoping splint elements; and d. releasable elements configured to lock the telescoping splint elements and the limb engaging elements against respective relative movement while the splint device is in a limb restraint position.

In a compact, economical and easily deployable embodiment the splint device comprises four major components, several of which may be identical, to facilitate manufacture and use. The splint device in this embodiment, is a longitudinally elongated device configured in an expandable (or retractable) telescopic length configuration, with maintained structural integrity sufficient to resist possible heavy loads and with reliable movement, positioning and positioning releasable locking, as needed. Though the device may be made of metal, engineered plastics, rather than metal as the material used in the splint device, provides advantages and enables effective use of MRI and x-ray machinery normally used to examine and diagnose patients with broken bones or fractures, without the necessity of removing the splint device.

In accordance with an embodiment of the invention, the splint device comprises a first track or slide member and second and third elongated riding or slider members movably held and positioned on the first track member in a plane adjacent and parallel thereto or in line therewith. The second and third elongated riding members are freely movable or rideable along a single longitudinal axis with expanded limits (and, in an embodiment, removable) being defined by non overlapping length of the first track member and second and third riding members. The compacted length for minimal limits is generally defined by either the length of the first track member or by the added length of the respective riding members when abutted or closely spaced. In economical embodiments, the second and third elongated riding members are identical in structure for interchangeable use. When the first and second riding members are moved to an extended or contracted position suitable for a splinting operation a releasable mechanism is activated between the first track member and either or both of the second and third riding members, to maintain the selected length. An example of the mechanism is that of interlocking teeth in the separate member which can be readily released as desired. In some embodiments, the release mechanism is shielded from accidental activation.

The compacted or minimal limits are ideally of a dimension small enough for the compacted splint device to be compacted (with release of the releasable mechanism) and stowed for transport in an EMT jump bag/kit. Operable limits and dimensions of the length of the splint device are defined by the lengths of the second and third elongated riding members plus the exposed distance of the first track member between separated second and third riding members. Generally, a minimal to maximum range length of about 18" to about 35" is adequate for EMT jump bag/kit stowing and for effective utilization on both arms around an elbow and legs around a knee.

The splint device further comprises a fourth component of two or more adjustable belt elements (with two being the minimum for splint device operable attachment to a patient-one or more on each riding member) which are used to affix the splint device to a patient in a proper splinting position, either in a straight immobilizing position or across a joint to immobilize relative movement of an arm or leg around the joint. The adjustable belt elements are fixedly fastened to one of the second and third elongated riding members and movably positioned through the first track member such as through a longitudinally extending slot or channel within the first track member.

In embodiments herein, the adjustable belt elements comprise terminal (relative to a central portion of the belt element) releasable connecting elements configured to be fixedly positioned through one of the second and third riding members and releasably, lockingly engaged with an outer surface of the respective second and third riding member. For patient comfort, the surfaces of the second and third riding member members which engage the releasable connecting elements, are recessed to prevent engagement of any extending part of the connecting elements with the patient, by enclosing them below the patient engaging surface levels.

In an embodiment herein, the adjustable belts elements comprise a hard plastic (or similar material) member base integrated with a releasable connecting element extending from a surface thereof for attachment to a riding member (non-releasable connecting elements are included herein but are generally not as desirable, since permanent attachment may affect stowability and maintenance of the splint device). The hard plastic member is attached at one end to a first end of an adjustable belt and releasably attached at another end to a second end of the belt such as with a quick release and deployable hook engagement. The second end of the belt is provided with a belt tightening mechanism to provide for adjustable belt tensioning on a patient's limb. Alternatively, the belt may be releasably attached to both ends or the belt is non-releasably attached to both ends of the hard base. In various embodiments the belt may be configured to be drawn tightly as desired or provided with hook and eye engagement and the like to provide appropriate sized attachment to a patient's limb.

In an embodiment, the releasable connecting element is comprised of an end beveled split post with an undercut wherein the split end is compressed for beveled insertion within an aperture of the respective riding member and wherein the undercut engages the peripheral surface of the aperture after the beveled head passes through the aperture, to effect the holding engagement. Release and removal of the split post is effected with finger compression of the split end and forcing the reduced diameter end back through the aperture. The beveled head is positioned below the outer surface of the respective riding members to prevent irritation of a patient coming in contact with any protruding heads.

Each of the riding members has between one (minimal) and four apertures (or other attachment sites) for connection of the connecting elements and attached belts for effective limb placement regardless. Four apertures or attachment sites are effective for the limb placement and immobilization, though more apertures for belt attachment are possible but generally with increased size of the splint device.

The belts may be attached to a patient on either side of the splint device with patient limb contact directly with the riding members or with the track member, as appropriate. To minimize patient discomfort, in a further embodiment, either or both the riding members and the track member may be provided with cushioning material on the contact surfaces thereof. Such cushioning material may be individually placed on each of the members. If a single cushioning member is placed on the surfaces of both the riding members, it should be capable of being stretched, without loss of elasticity, for a distance sufficient to span the overall length of the riding members in a minimal length position to a maximum extended length.

In accordance with the method used in the present invention with utilization of the above described splint device, the splint is deployed on the limb of a patient in need thereof by one person with the steps of:

a) extending the length of an elongatable compacted splint device from storage, in a small length position, to a length required to fix a limb into an immobilized position;

b) locking the length of the compacted splint device to the required length;
c) attaching at least two straps used to hold the splint device in position to fix the limb in an immobilized position with an insertion connection to the splint device;
d) placing the splint device on the limb and encircling the limb with the at least two straps, and
e) tightening the straps to an appropriate tightness.

It is understood that the above objects, features and advantages are only illustrative of the invention and that further objects, features and advantages will become more evident from the following discussion and drawings in which:

SHORT DESCRIPTION OF THE DRAWINGS

FIG. 8 is a perspective view of the track or slider mechanism apart from the splint device;

FIGS. 9a and 9b are perspective top and bottom views of the belt holding base with releasable connecting element respectively;

FIGS. 12a and 12b are perspective views of a belt element having a single removable connection of a belt to a base with base and connecting element in outward and inward positions respectively;

FIGS. 14a and 14b are views of a base element with connection element and as attached to adjustable hook and eye elements respectively;

Figure 1:
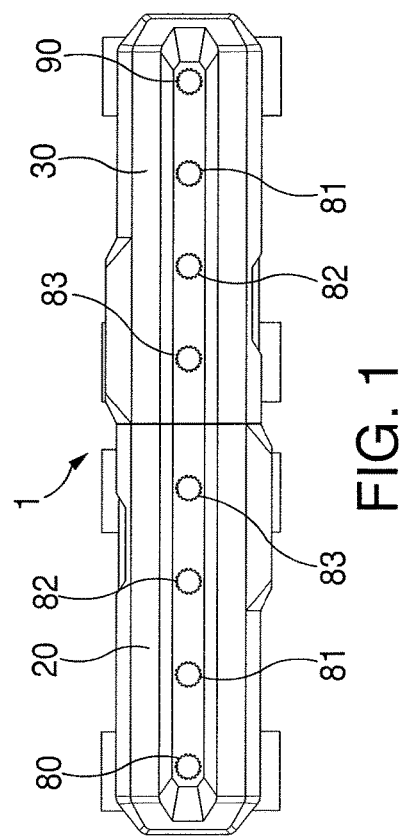
FIG. 1 is a top view of the splint device in a minimal closed position.
Figure 15C:
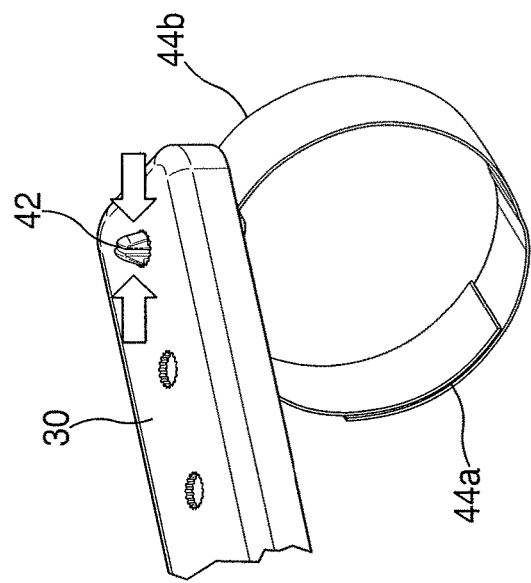
Figure 15B:
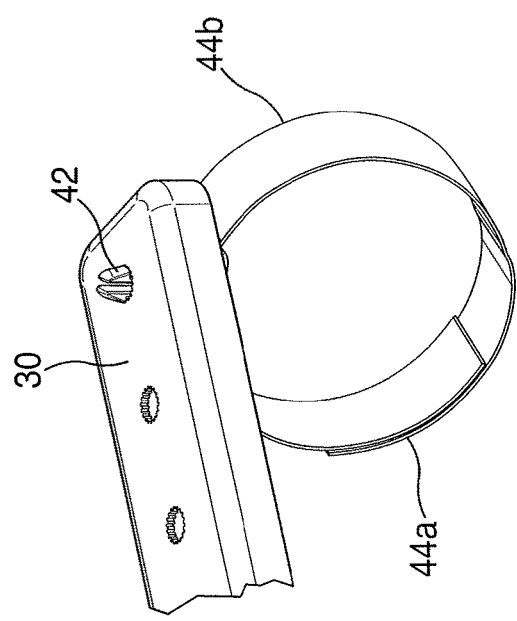
Figure 15A:
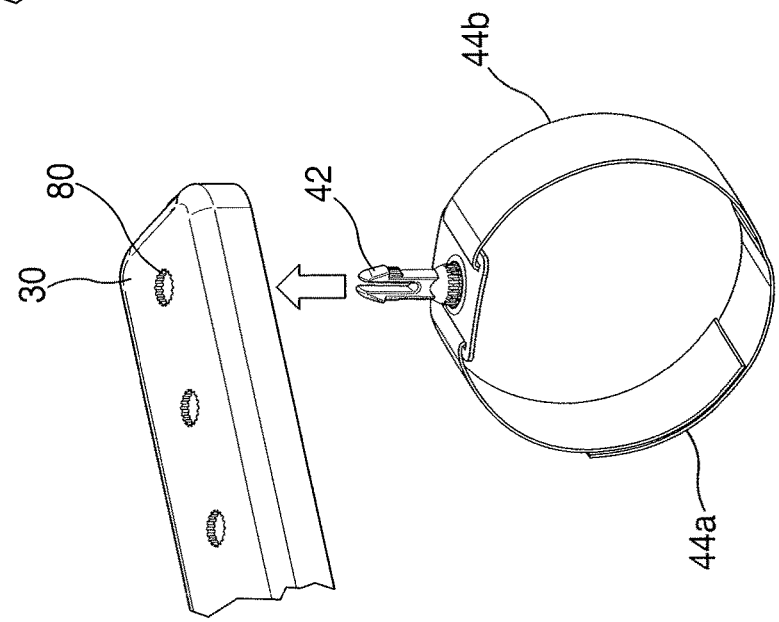
Figure 19A:
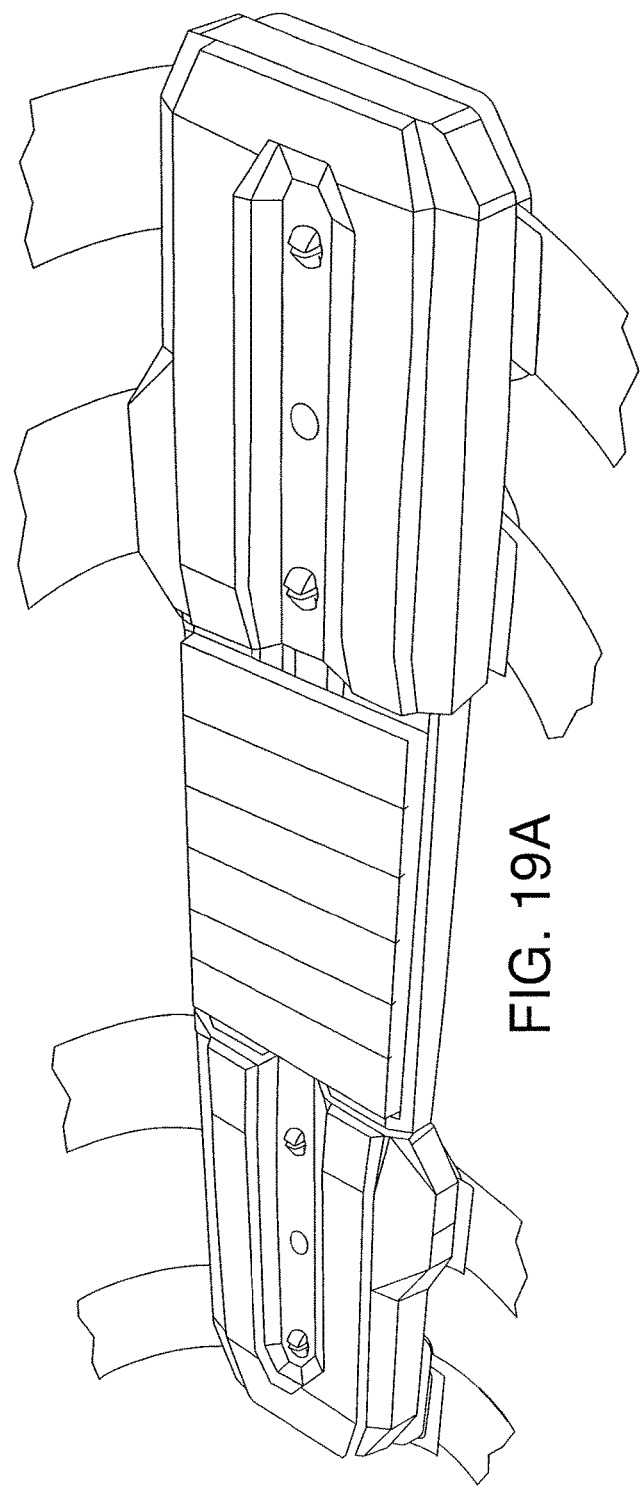
Figure 19B:
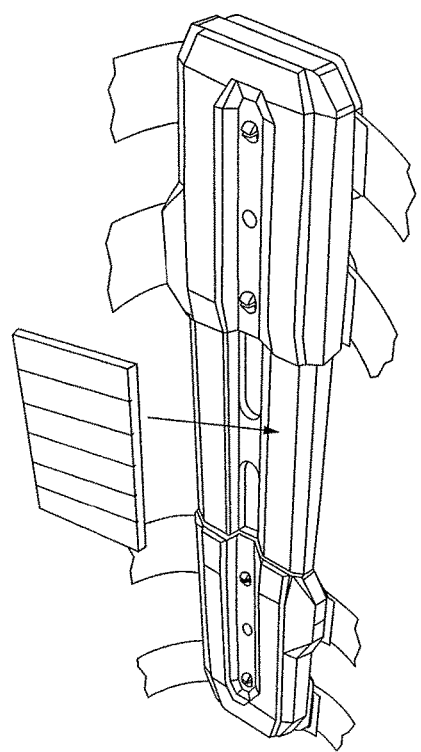
Figure 21A:
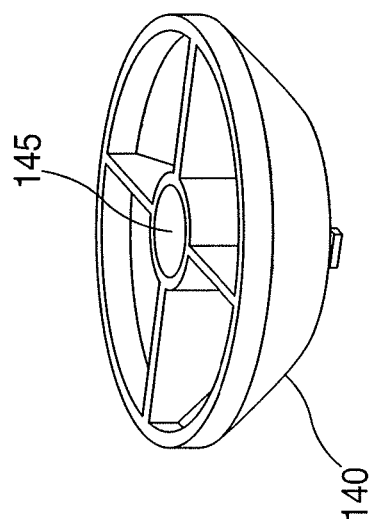
Figure 21B:
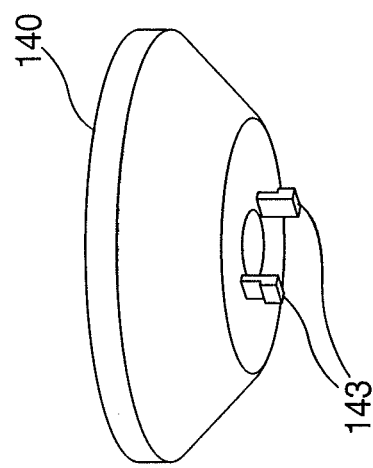
Figure 20:
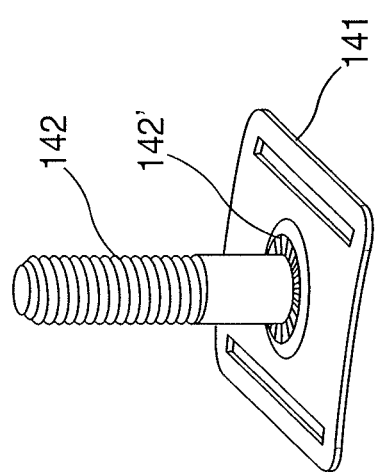
Figure 22C:
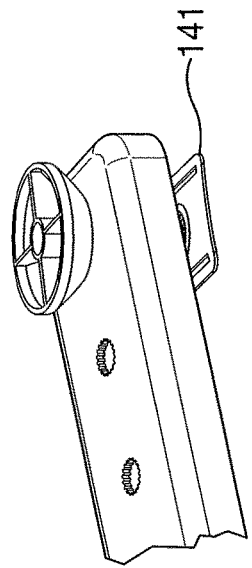
Figure 22B:
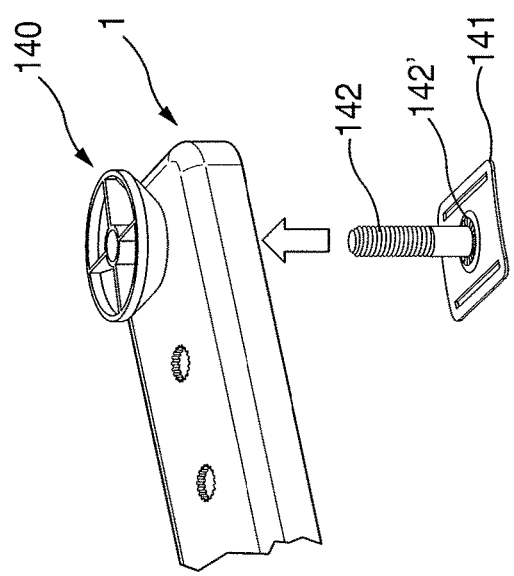
Figure 22A:
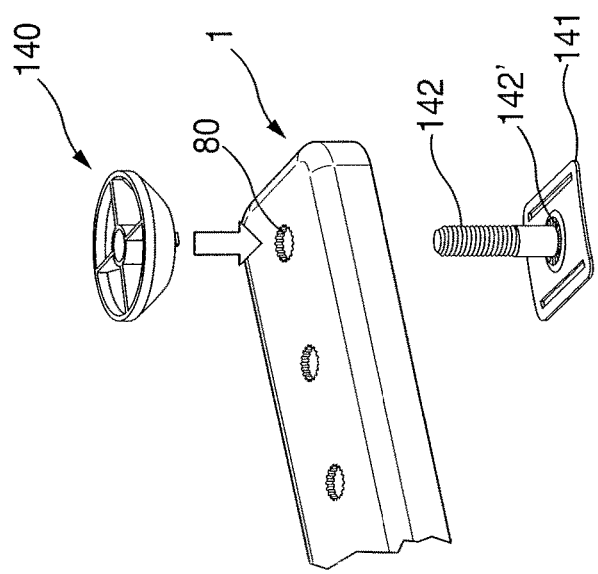

FIGS. 15a-c depict the sequential attachment and removal of the belt element of FIG. 14b from a riding member of the splint device;

FIG. 16 is a cushioning cover for the riding members of the splint device;

FIGS. 17a and 17b are top views of the cushioning cover positioned on the riding members in the minimal length and maximal length respectively;

FIG. 17c is a side view of FIG. 17b;

FIGS. 18a-c are top views of another cushioning cover embodiment with spandex form pads;

FIGS. 19a-b are a sequential depiction of placement of removable neoprene cushioning strips on an exposed surface of the track member after being locked into a deployment position FIG. 20 depicts an alternative connecting element of a threaded stud, FIGS. 21a and 21b are upper perspective and lower perspective views of a threaded nut/knob used with the connecting element of FIG. 20; and FIGS. 22a-c depict the sequential engagement of connecting element and threaded nut/knob of FIGS. 20 and 21a-b with the splint of FIG. 1.

DETAILED DESCRIPTION

Figure 2A:
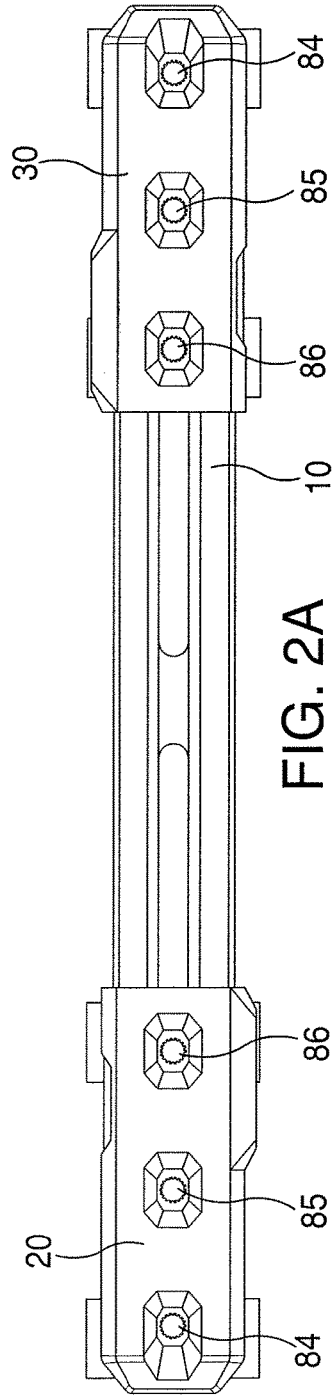
FIGS. 2a and 2b are top views of the splint device with three aperture and four aperture embodiments for possible attachment of three or four holding belts on each of the riding members respectively.
Figure 2B:
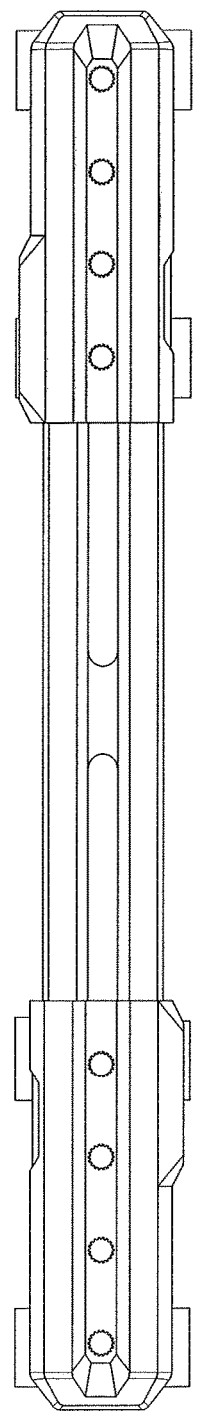
Figure 3:
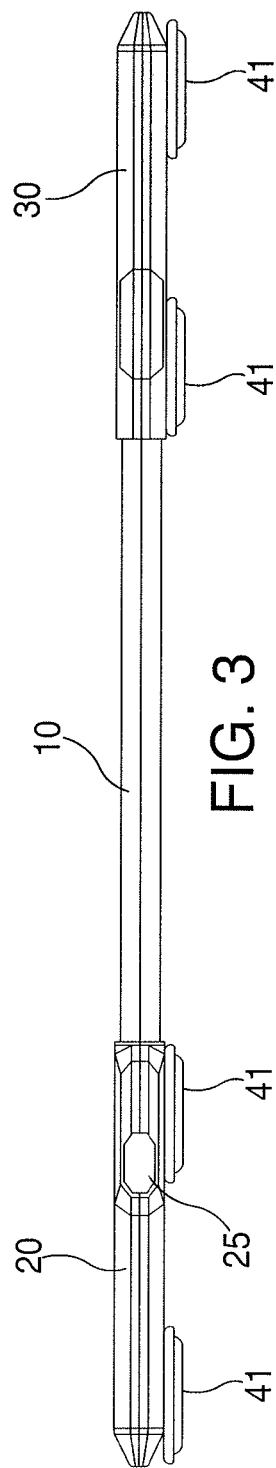
FIG. 3 is a side of the splint device showing the position disengagement button for one of the riding members with a corresponding disengagement button on the opposite (non visible) side.
Figure 6A:
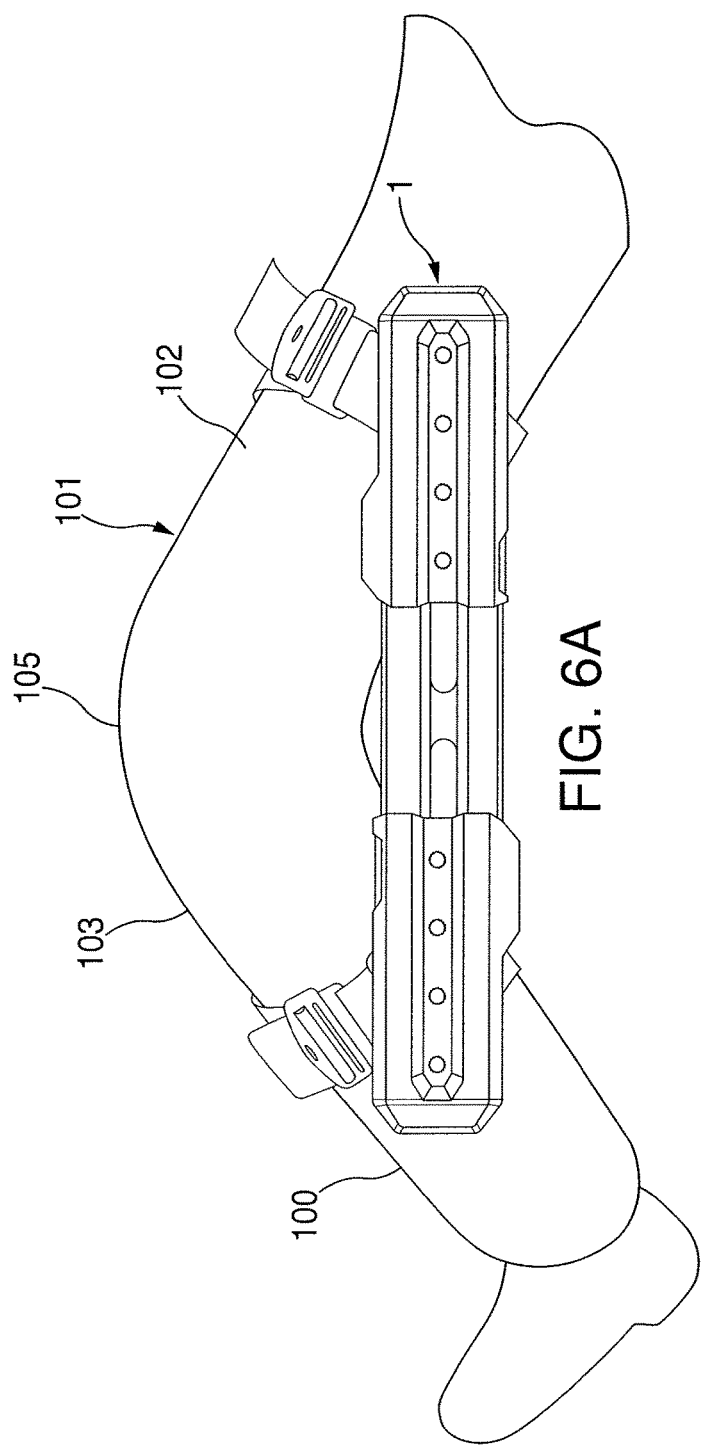
FIGS. 6a and 6b depict deployment of the splint device on a patient's leg with a bent limb configuration and with a straight limb immobilized configuration respectively.

With reference to the drawings, FIG. 1 shows the splint device 1 in the minimal closed position, as generally used for stowing the splint device in an EMS bag/kit. Riding members 20 and 30, which are longitudinally movable relative to each other, are shown abutted with one another in a closed or minimal length position. As shown, each of the riding members 20 and 30 has four apertures 80-83, used for connection to a belt member for connection to a patient, as shown in FIGS. 1, 2b, 4, 6a, 6b, and 10. Riding members with three apertures 84-86 are shown in FIGS. 2a, 7, and 19.

Figure 10:
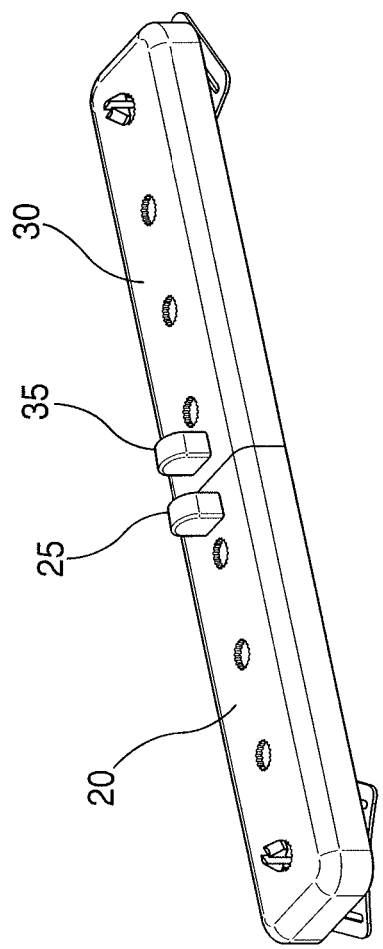
FIG. 10 depicts a the splint device with an alternative position locking and release element.

Riding members 20 and 30 are shown as slidingly seated on track member 10, in FIGS. 2a, 2b, 3 and 4, with riding members 20 and 30, being identical in structure and positioned on track member 10, in mirror image placement. Button 25 in FIG. 7, on riding member 20 (riding member 30, which is structurally identical to riding member 30 has a similar button, which is not visible) activates and deactivates engagement of tooth 26 into and out of engagement with teeth or tracks 16 on track member 10, to effect position fixing and position disengagement between the respective riding members 20 and 30 and the track member 10, as seen in FIGS. 7 and 8. FIG. 10 shows an alternative position locking control with pull tabs 25 and 35 on riding members 20 and 30 respectively to control position locking and releasing with minimized accidental release activation.

Figure 4:
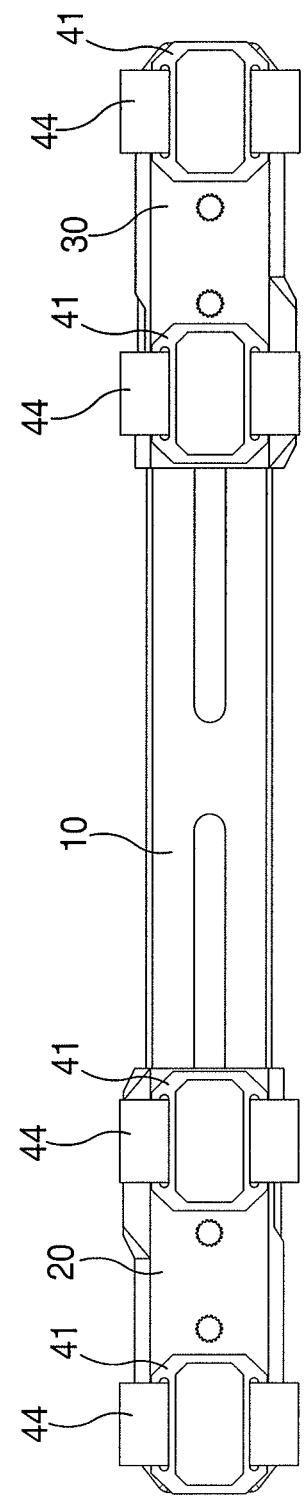
FIG. 4 is a top view of a splint device with four holding belts inserted from the riding member side.
Figure 11B:
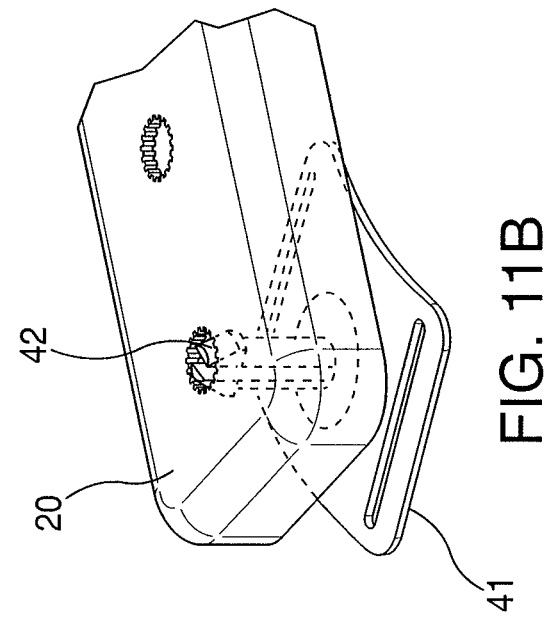
FIGS. 11a and 11b are partial views of the insertion of a connecting element at different position stages respectively.
Figure 11A:
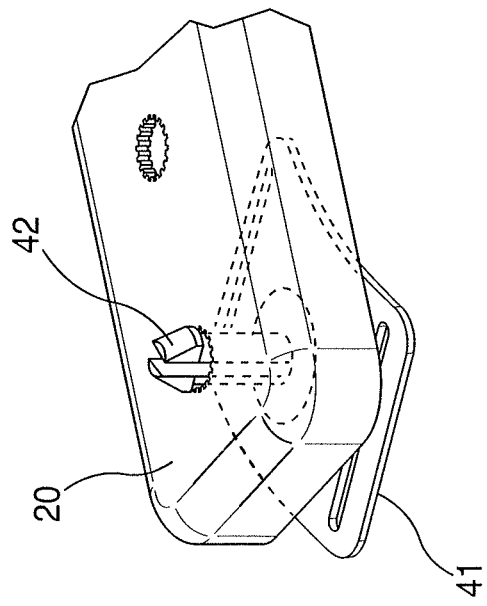

FIG. 4 shows attachment of belt base 41 to an aperture of a riding member with FIGS. 9a and 9b and 14a and 14b showing belt base 41 with connector 42 which is used to connect the belt base 41 to a riding member with the base belt 41 (and connected belt 44, 44a and 44b—in FIGS. 12a, 12b, 13a, 13b and 14b) is longitudinally movable with movement of the riding member to which it is attached. The connector 42 in FIGS. 14a and 14b is provided with a ridged base 42' which interacts with corresponding engaging ridges in FIGS. 11a and 11b to enable rotational positioning of the belt base 41 (with attached belt or strap 44, 44a and 44b) for rotated positioning on a patient as shown in FIG. 6a. Track member 10 has channels a and b as shown in FIG. 8 such that when riding members 20 and 30 are positioned thereon, channels a and b align with the apertures 80-83 or 84-86 whereby connector 42 passes through one of the channels and corresponding aperture starting either from the track member side as in FIG. 6a or from the riding member side as in FIG. 6. FIGS. 15a-c illustrate a sequential insertion of the connector 42 and removal from the splint device 1.

FIGS. 20 and 21a and 21b depict an alternative connecting element which comprises a threaded stud 142 on base 141 in FIG. 20, which is adapted to be engaged with threaded nut/knob 140 shown in FIGS. 21a and 21b to effect connection of a limb engaging belt or strap with the splint with a finer position adjustment. Nut 140 is conically shaped to provide enhanced manual manipulation by an EMT. As shown in FIG. 22a the circular snaps 143 at the base of the nut 140 are into aperture 80 of the splint 1 to hold it in place as shown in FIG. 22b while threaded stud 142 is inserted into aperture 80 into engagement with the threads of nut 140 in aperture 145. At the base of the threaded stud 142 there is a serrated face 142' which is brought into engagement with a corresponding serrated face on the splint 1 at the bottom peripheral surface of the aperture 80 (not shown). The strap holding base 141 is maneuvered into an ideal holding position and locked into the position with tightening of the nut 140 until the serrated faces of the splint 1 and threaded stud engage.

Figure 5:
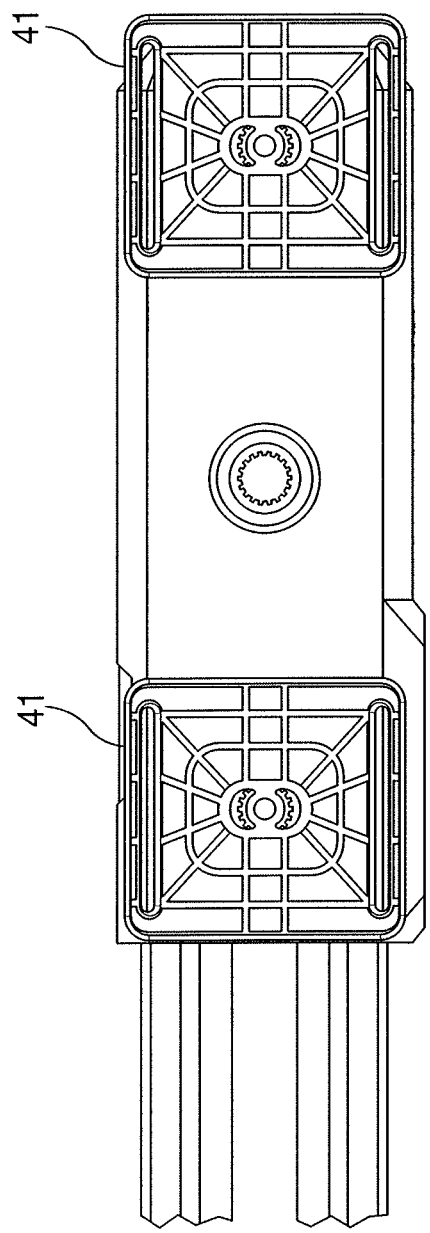
FIG. 5 is a partial view of a belt holding member as attached to a riding member via an aperture therein.
Figure 6B:
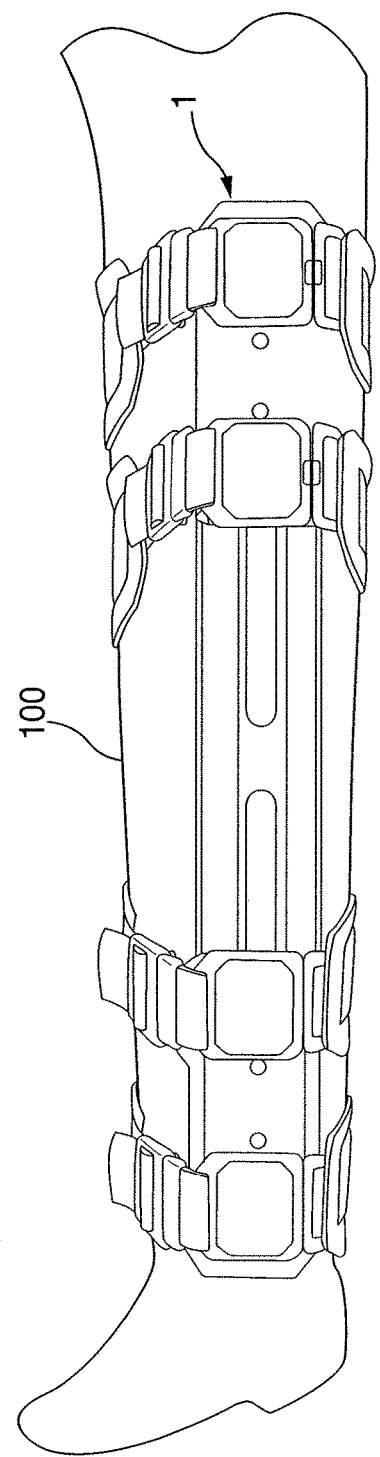
Figure 7:
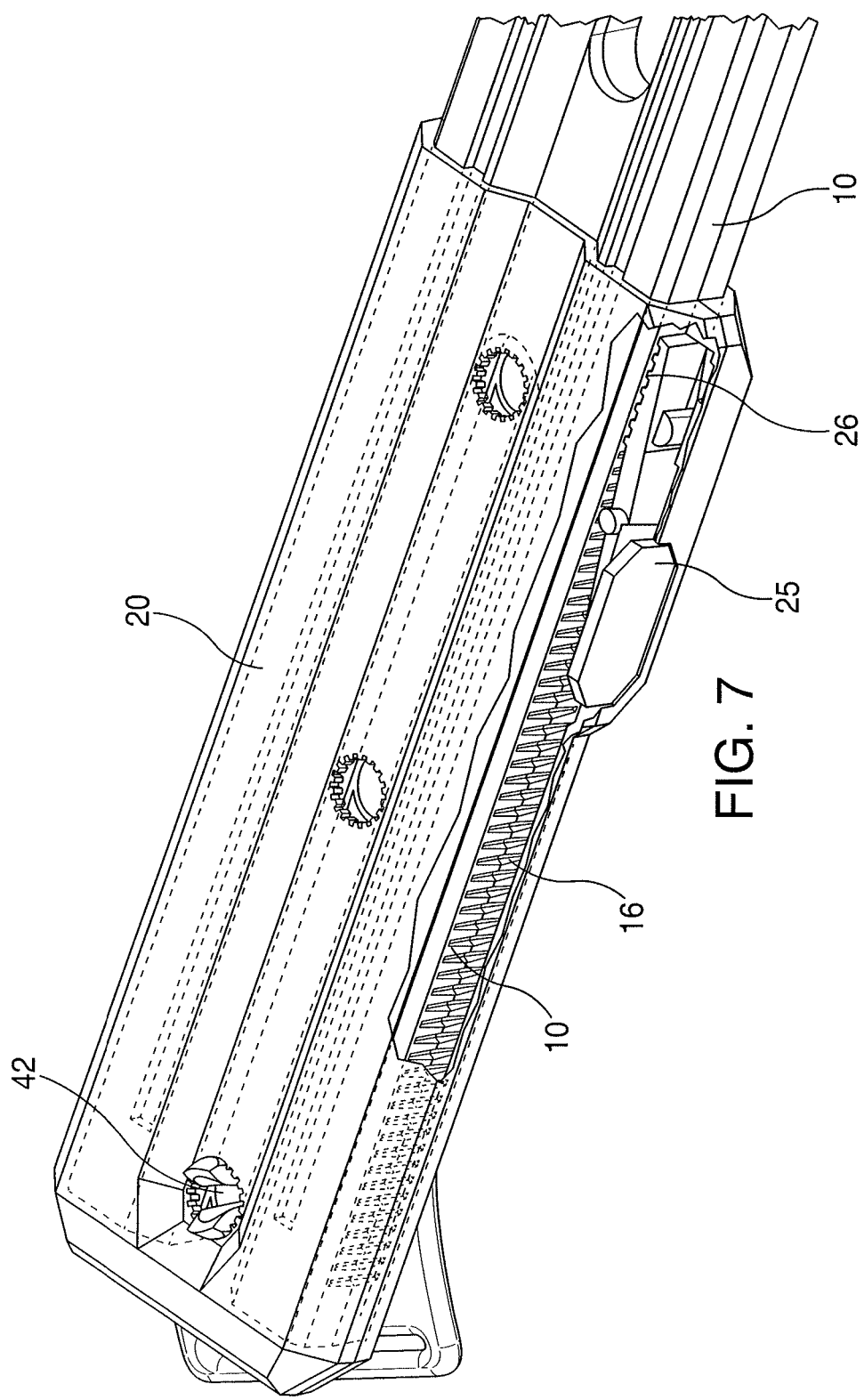
FIG. 7 is a partial perspective view of the splint device with attachment of the connecting element from the track member side through a slot in the track member and into an aperture of a riding member to support a belt holder and a view of the positioning connecting and releasing mechanism.

FIGS. 6a and 6b depict the splint device 1 in respective different extension lengths for attachment to immobilize a limb 101 (across thigh 102 and shin 103) of leg 100 around bent knee 105 (FIG. 5a) and for straight attachment on leg 100 (FIG. 5b).

For attachment to a patient as in FIGS. 6a and 6b, strap or belt 44 is attached to a base 41 and connecting member 42 in FIGS. 12a and 12b and FIGS. 13a and 13b, with FIGS. 12a and 12b showing a fixed rotatable attachment of a belt end 47 with the connector base 41 and a hook-loop connection 43 and 43a via short tether 44' attached to the connector base 41. Standard belt tightening is effected with adjustment loop 46. Neoprene cushion 49 is a removable option in the embodiments shown in FIGS. 12a, 12b, 13a and 13b.

Figure 13A:
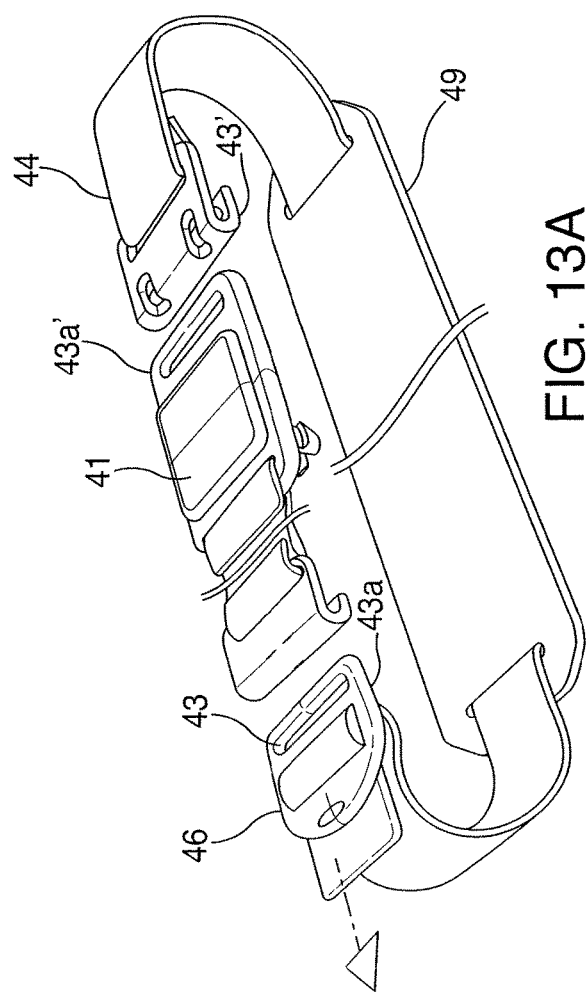
FIGS. 13a and 13b are similar to the perspective view of FIGS. 12a and 12b but with double removable connections between the belt and the base.
Figure 13B:
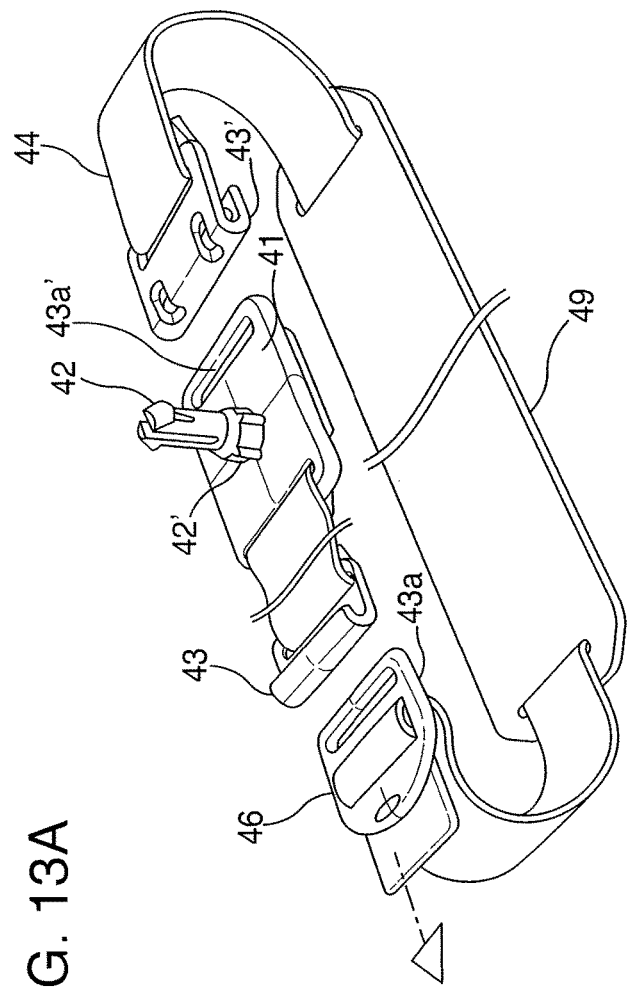

In FIGS. 13a and 13b connection between the belt 44 and the connector base 41 is via two hook loop connection with a first 43 and 43a as in FIGS. 12a and 12b and a second direct hook-loop connection between 43' and 43a' which replaces the rotatable attachment 47 in the embodiment of FIGS. 12a and 12b. Rotation for selective attachment to a riding member is effected by reversal of the hook attachments, as shown.

FIGS. 14a and 14b show another embodiment of a belt attachment with the connector base 41 being non-removably attached to straps 44a and 44b with a hook and eye (commonly known as Velcro®) attachment. Reversal of direction of attachment between straps 44a and 44b serves to "rotate" the belt for attachment to the riding member.

For patient comfort various cushioning elements are shown in FIGS. 16, 17a-c, 18a-c and 19, which are removable placed over the riding members as stretchable cover padding 50 in FIG. 16, which is placed over the full length of the splint device 1 on top of the riding members 20 and 30 in a minimal length configuration in FIG. 17a to a stretched maximum length in FIG. 17b. FIG. 17c shows that the stretchable cover padding leaves the control button and sides of the splint device open. FIGS. 18a-c show a similar stretchable cover 60 and placement made of spandex material with form pad 61 inside. In all of the embodiments in FIGS. 17a-c and 18a-c, the padding is used to cover the side of the splint device where the heads of the connectors 42 protrude. FIGS. 19a and 19b show the placement of removable neoprene strips in exposed portions of the track member for cushioning when the split device is in an extended position.

It is understood that the above description and embodiments are merely illustrative of the invention and are not construed to be limitations on the present invention. Changes such as in the structure, configuration and interrelation of the elements, are possible without departing from the scope of the invention as defined in the following claims.

What is claimed is:

1. An expandable and contractible longitudinally elongated splint device for the restraint of human or animal limbs into any of straight or bent immobile positions, with substantial prevention of movement from the immobile positions, the splint device comprising:
   i. at least two longitudinally extending splint elements, slidingly fastened to each other along a co-extensive central longitudinal axis, and configured to be respectively moved relative to each other in a longitudinal direction along the longitudinal axis to obtain a desired longitudinal length of the elongated splint;
   ii. interfitting engaging and disengaging tooth elements in each of adjacent splint elements configured to be releasably lockingly engaged with each other to permit relative sliding movement between the splint elements and releasably lockingly engaged at desired relative positions between the adjacent splint elements to maintain the splint elements at the desired longitudinal length with respective longitudinal movement;
   iii. at least two releasable adjustable limb engaging and holding, belt, strap or clamp elements, with each comprising a connecting member thereon and extending therefrom in a direction away from the limb engaging and holding elements, the connecting member being configured for insertion and releasable locking into at least one of multiple apertures positioned and substantially aligned along the co-extensive central longitudinal axis of the longitudinal length of the splint elements, to thereby securely attach the limb engaging elements in a desired longitudinally spaced apart position on the splint elements and wherein respective connecting members and splint elements comprise releasably engaging teeth elements which permit rotation of the respective limb engaging elements relative to the splint element to respective desired rotated limb engaging and holding positions and with releasable locking elements to lock the limb engaging and holding teeth elements in the desired rotated positions against respective relative rotational movement on the splint elements to which they are respectively connected, while the splint elements are maintained in the longitudinal direction along the co-extensive central longitudinal axis in any of a straight or bent limb restraint position.

2. The longitudinally elongated splint device of claim 1, wherein the at least two-splint elements are telescoping and movably fastened to each other and configured to be movable in the longitudinal direction to obtain the desired length of the elongated splint.

3. The longitudinally elongated splint device of claim 2, wherein the telescoping splint elements are movably positioned relative to each other along a single longitudinal axis.

4. The longitudinally elongated splint device of claim 2, wherein the telescoping splint elements are movably positioned relative to each other along parallel planes and are slidable relative to each other.

5. The longitudinally elongated splint device of claim 1, wherein the fastened splint elements are releasably attached to each other and are added or removed to provide the desired length.

6. The longitudinally elongated splint device of claim 1, comprising:
   a. an elongated track member, with opposite ends, extending along a longitudinal axis;
   b. at least two elongated riding members attachable onto the track member at the opposite ends respectively, with the riding members being configured to ride on the elongated track member along the longitudinal axis toward and away from each other to provide a desired expanded or contracted length of the splint device, with the track member and riding members comprising the splint elements; and c. the position retention and releaseable locking engaging tooth elements between the track member and the riding members configured to maintain the desired expanded or contracted length position of the splint device and for the release thereof.

7. The longitudinally elongated splint device of claim 1, wherein the splint elements comprise the longitudinally spaced apertures and the limb engaging elements comprise stud members configured to be inserted into selected spaced apertures respectively and releasably locked therein to provide the desired spaced apart position.

8. The longitudinally elongated splint device of claim 7 wherein the stud member comprises an integrated compressible bevel with undercut structure to provide the releasable locking.

9. The longitudinally elongated splint device of claim 1, wherein the releasable elements to lock the splint elements and the limb engaging elements against respective relative movement while the splint device is in a limb restraint position, comprise coactive engaging teeth elements between a surface of the splint element and limb engaging elements.

10. A method for deploying a splint on a limb of a human or animal in need thereof with the steps of:

a. extending or contracting the length of the elongatable compacted splint device of claim 1 to a length required to fix the limb into any of a straight or bent immobilized position;

b. locking the length of the compacted splint device to the required length with cooperatively engaging tooth elements;

c. attaching at least two straps used to hold the splint device in position to fix the limb in the straight or bent immobilized position with an insertion connection of the connection members of the straps into the respective apertures of the splint device;

d. placing the splint device on the limb with rotating and locking the two straps in a desired straight or bent limb immobilizing position, if necessary, and encircling the limb with the at least two straps, and e. tightening the straps to an appropriate tightness.

* * * * *